(12) United States Patent
Liang et al.

(10) Patent No.: US 7,929,151 B2
(45) Date of Patent: Apr. 19, 2011

(54) INTRA-ORAL CAMERA FOR DIAGNOSTIC AND COSMETIC IMAGING

(75) Inventors: Rongguang Liang, Penfield, NY (US); Jean-Marc Inglese, Bussy Saint Georges (FR)

(73) Assignee: Carestream Health, Inc., Rochester, NY (US)

( * ) Notice: Subject to any disclaimer, the term of this patent is extended or adjusted under 35 U.S.C. 154(b) by 524 days.

(21) Appl. No.: 11/972,907

(22) Filed: Jan. 11, 2008

(65) Prior Publication Data

US 2009/0181339 A1 Jul. 16, 2009

(51) Int. Cl.
*G01B 11/24* (2006.01)
(52) U.S. Cl. ............ 356/601; 356/51; 356/407; 433/29; 382/128
(58) Field of Classification Search .......... 356/601–613, 356/300, 317, 318, 326, 407; 433/29, 215; 600/112, 476; 382/132, 128, 165, 164
See application file for complete search history.

(56) References Cited

U.S. PATENT DOCUMENTS

| | | | |
|---|---|---|---|
| 4,290,433 A | 9/1981 | Alfano | |
| 4,479,499 A | 10/1984 | Alfano | |
| 4,881,811 A | 11/1989 | O'Brien | |
| 5,040,539 A | 8/1991 | Schmitt et al. | |
| 6,024,562 A | 2/2000 | Hibst et al. | |
| 6,132,210 A | 10/2000 | Lehmann | |
| 6,215,893 B1 * | 4/2001 | Leshem et al. ................ | 382/128 |
| 6,231,338 B1 | 5/2001 | deJosselin de Jong et al. | |
| 6,305,933 B1 | 10/2001 | Lehmann | |
| 6,571,118 B1 * | 5/2003 | Utzinger et al. .............. | 600/476 |
| 6,672,868 B1 | 1/2004 | Momot et al. | |
| 6,899,675 B2 * | 5/2005 | Cline et al. .................... | 600/160 |
| 7,030,986 B2 | 4/2006 | Overbeck et al. | |
| 7,064,830 B2 * | 6/2006 | Giorgianni et al. ........... | 356/402 |
| 7,253,894 B2 * | 8/2007 | Zeng et al. .................... | 356/326 |
| 2005/0003323 A1 | 1/2005 | Katsuda et al. | |
| 2005/0074718 A1 | 4/2005 | Graham et al. | |
| 2006/0040230 A1 * | 2/2006 | Blanding et al. ................ | 433/26 |
| 2006/0239526 A1 * | 10/2006 | Jonusauskas et al. ........ | 382/128 |
| 2007/0099148 A1 | 5/2007 | Wong et al. | |
| 2007/0134615 A1 | 6/2007 | Lovely | |
| 2007/0248931 A1 * | 10/2007 | Wong et al. ..................... | 433/29 |
| 2008/0056551 A1 * | 3/2008 | Wong et al. ..................... | 382/132 |
| 2008/0062429 A1 * | 3/2008 | Liang et al. ..................... | 356/497 |
| 2008/0063998 A1 * | 3/2008 | Liang et al. ..................... | 433/29 |
| 2008/0090198 A1 * | 4/2008 | Liang et al. ..................... | 433/29 |
| 2008/0118886 A1 * | 5/2008 | Liang et al. ..................... | 433/29 |
| 2008/0177140 A1 * | 7/2008 | Cline et al. .................... | 600/112 |
| 2009/0118622 A1 * | 5/2009 | Durkin et al. ................. | 600/473 |
| 2009/0131800 A1 * | 5/2009 | Liang ............................. | 600/476 |
| 2009/0274998 A1 * | 11/2009 | Wong et al. ................... | 433/215 |
| 2009/0297003 A1 * | 12/2009 | Wong et al. ................... | 382/128 |
| 2010/0201986 A1 * | 8/2010 | Inglese et al. ................ | 356/407 |

FOREIGN PATENT DOCUMENTS

| | | |
|---|---|---|
| WO | WO 2004/012593 | 2/2004 |
| WO | WO 2005/080929 | 9/2005 |
| WO | WO 2007/053293 | 5/2007 |

* cited by examiner

*Primary Examiner* — Hoa Q Pham

(57) ABSTRACT

An apparatus for obtaining images of a tooth comprises at least one image sensor disposed along an optical axis to take polarized reflectance image and fluorescence image, at least one broadband illumination apparatus for reflectance imaging, and a narrow-band ultraviolet illumination apparatus for fluorescence imaging. In order to remove the specular reflection, one or more polarization elements are disposed along the optical axis. A filter is disposed along the optical axis to block narrow-band ultraviolet light, and a switch for selecting one of the operation modes.

14 Claims, 16 Drawing Sheets

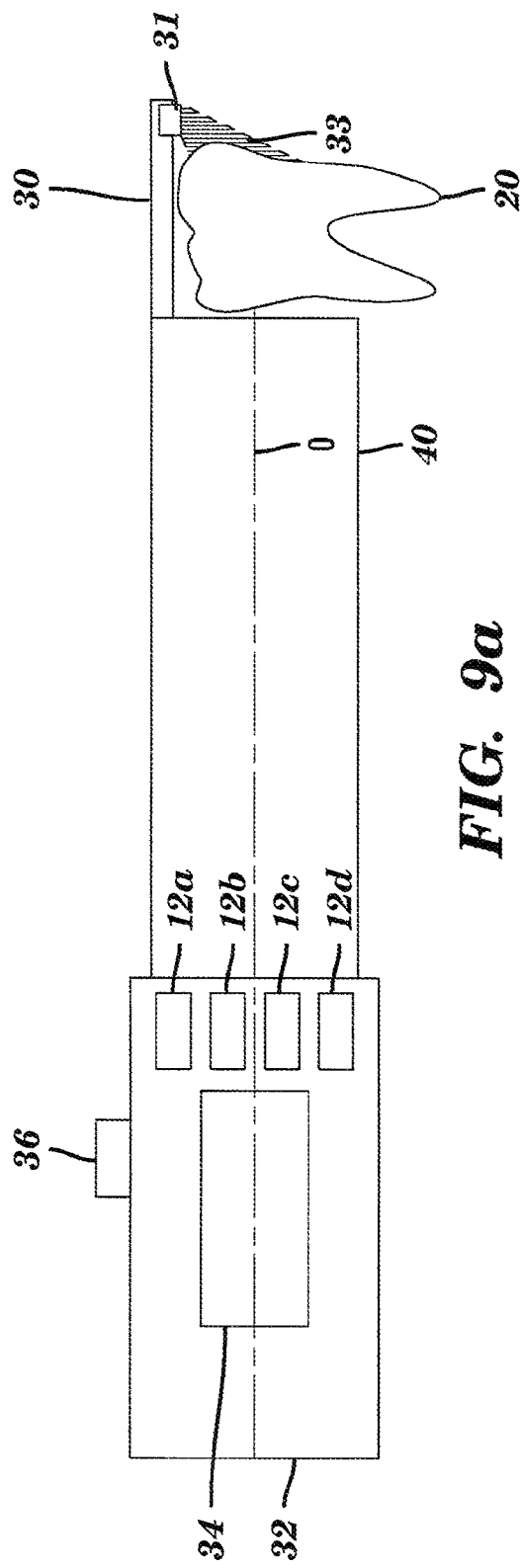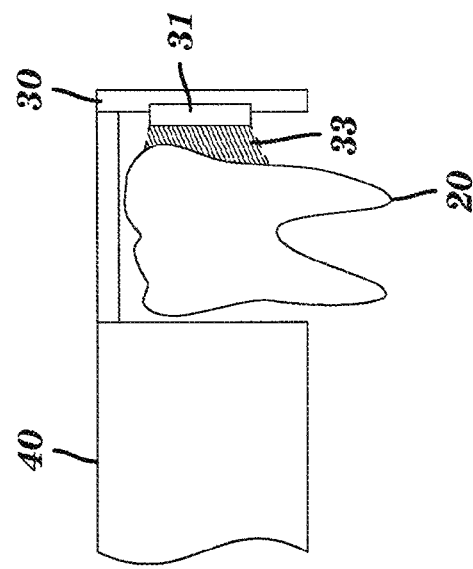
FIG. 9a
FIG. 9b

INTRA-ORAL CAMERA FOR DIAGNOSTIC AND COSMETIC IMAGING

CROSS-REFERENCE TO RELATED APPLICATIONS

The present application is related to U.S. Patent Application Publication 2007/0099148, entitled METHOD AND APPARATUS FOR DETECTION OF CARIES, filed Oct. 31, 2005 in the names of Victor C. Wong, Rongguang Liang, and Donna Rankin-Parobek; U.S. Patent Application Publication 2007/0248931, entitled OPTICAL DETECTION OF DENTAL CARIES filed Apr. 21, 2006 in the names of Victor C. Wong, Rongguang Liang, Michael A. Marcus, Paul O. McLaughlin, and David Patton; and U.S. patent application Ser. No. 11/623,804, entitled SYSTEM FOR EARLY DETECTION OF DENTAL CARIES filed Jan. 17, 2007 in the names of Peter D. Burns, Victor C. Wong, Mark E. Bridges and Rongguang Liang.

FIELD OF THE INVENTION

This invention generally relates to methods and apparatus for dental imaging and more particularly relates to an intra-oral camera apparatus that includes capabilities for caries detection as well as for shade matching.

BACKGROUND OF THE INVENTION

Digital imaging has been adapted to serve dentistry for both diagnostic and cosmetic purposes. For example, there have been a number of dental imaging systems developed for diagnosis of dental caries in its various stages, capable of assisting in this diagnostic task without the use of x-rays or other ionizing radiation. One method that has been commercialized employs fluorescence, caused when teeth are illuminated with high intensity blue light. This technique, termed Light-Induced Fluorescence (LIF), operates on the principle that sound, healthy tooth tissue yields a higher intensity of fluorescence under excitation from some wavelengths than does de-mineralized tooth tissue that has been damaged by caries infection. The strong correlation between mineral loss and loss of fluorescence for blue light excitation is then used to identify and assess carious areas of the tooth. A different relationship has been found for red light excitation, a region of the spectrum for which bacteria and bacterial by-products in carious regions absorb and fluoresce more pronouncedly than do healthy areas. Utilizing this behavior, U.S. Pat. No. 4,290,433 entitled "Method and Apparatus for Detecting the Presence of Caries in Teeth Using Visible Luminescence" to Alfano discloses a method to detect caries by comparing the excited luminescence in two wavelengths. The use of fluorescence effects for caries detection is also described in U.S. Pat. No. 6,231,338 entitled "Method and Apparatus for the Detection of Carious Activity of a Carious Lesion in a Tooth" to de Josselin de Jong et al.

Reflectance characteristics of visible light have also been used for oral caries diagnosis. For example, U.S. Pat. No. 4,479,499 entitled "Method and Apparatus for Detecting the Presence of Caries in Teeth Using Visible Light" to Alfano describes a method to detect caries by comparing the intensity of the light scattered at two different wavelengths. Commonly assigned U.S. Patent Application Publication 2007/0099148, previously mentioned, describes an improved method for caries detection that combines both fluorescence and reflectance effects.

Among commercialized products for diagnostic dental imaging using fluorescence behavior is the QLF Clinical System from Inspektor Research Systems BV, Amsterdam, The Netherlands, described in U.S. Pat. No. 6,231,338. Using a different approach, the Diagnodent Laser Caries Detection Aid from KaVo Dental GmbH, Biberach, Germany, described in U.S. Pat. No. 6,024,562, detects caries activity monitoring the intensity of fluorescence of bacterial by-products under illumination from red light. Other commercial products, such as the DIFOTI system from Electro-Optical Sciences, Irvington, N.Y., described in U.S. Pat. No. 6,672,868, use transmission of light through the tooth structure for diagnostic imaging.

Diagnostic imaging methods have been developed for use with hand-held devices. For example, U.S. Patent Application Publication 2005/0003323, entitled "Diagnostic Imaging Apparatus" by Naoki Katsuda et al. describes a complex hand-held imaging apparatus suitable for medical or dental applications, using fluorescence and reflectance imaging. The '3323 Katsuda et al. disclosure shows an apparatus that receives the reflection light from the diagnostic object and/or the fluorescence of the diagnostic object with different light irradiation. However, with such an approach, any unwanted specular reflection produces false positive results in reflectance imaging. Moreover, with the various illumination embodiments disclosed, the illumination directed toward a tooth or other diagnostic object is not uniform, since the light source is in close proximity to the diagnostic object.

Cosmetic dentistry has also taken advantage of digital imaging capability to some extent, primarily for shade-matching in tooth restoration or replacement. There have been numerous solutions proposed for providing some form of automated shade matching to assist the dentist. A few examples are given in U.S. Pat. Nos. 6,132,210 and 6,305,933, both entitled "Tooth Shade Analyzer System and Methods" both to Lehmann; and in U.S. Patent Application Publication No. 2005/0074718 entitled "Tooth Shade Scan System and Method" to Graham et al. Apparatus solutions for cosmetic imaging are outlined, for example, in International Publication No. WO2005/080929 entitled "Equipment and Method for Measuring Dental Shade" by Inglese and in U.S. Pat. No. 4,881,811 entitled "Remote Color Measurement Device" to O'Brien. Commercialized hand-held products directed to shade matching include the ShadeScan™ system from Cynovad, Montreal, Calif., described in Cynovad brochure 1019 of February 2002; and the Shade-Rite™ Dental Vision System from X-Rite Inc., Grandville, Mich., described in U.S. Pat. No. 7,030,986. Notably, hand-held shade-matching systems are not designed for ease of access to any but the front teeth. Conventional shade-matching techniques can match tooth color acceptably, but may not provide enough data for providing a substitute tooth that appears real and exhibits some amount of translucence. This is largely because conventional cosmetic imaging systems are directed primarily to color matching, but provide insufficient information on tooth translucency and surface texture. For cosmetic systems that measure translucency, little or no attention is paid to uniformity of illumination. This results in an uneven distribution of light and reduces the overall accuracy of the system for measuring tooth translucency.

In spite of the growing range of imaging devices that is now available to the dental practitioner for diagnostic and cosmetic purposes, there is still room for improvement. Diagnostic imaging apparatus and shade-matching systems are still separate pieces of equipment, each system having its own requirements for system optics. To a large extent, this is the result of their different functions, affecting numerous components from illumination, light shaping, and imaging subsystems. For example, the illumination requirements for diagnostic imaging, largely using fluorescence effects, differ significantly from those of cosmetic imaging, which largely employs reflective light. Specular reflection can be undesirable for both diagnostic and cosmetic imaging, but must be compensated in different ways for each type of imaging. Image sensing, the use of polarization and spectral content, and other features further differentiate diagnostic from cosmetic systems. Thus, it would be advantageous to provide an intra-oral camera that could be used for both diagnostic and cosmetic functions.

SUMMARY OF THE INVENTION

An object of the present invention is to provide improved apparatus and methods for dental imaging. With this object in mind, the present invention provides an apparatus for obtaining an image of a tooth comprising at least one image sensor disposed along an optical axis; at least one broadband illumination apparatus for reflectance imaging; a narrow-band ultraviolet illumination apparatus for fluorescence imaging; one or more polarization elements disposed along the optical axis to eliminate specular reflection; a filter disposed along the optical axis to block narrow-band ultraviolet light; and a switch for selecting one of the operation modes of reflectance and fluorescence imaging.

An embodiment of the method of the invention is useful for obtaining images of a tooth for cosmetic imaging and comprises steps of directing light from the light source to tooth for obtaining a monochromatic image for translucency measurement; directing polarized visible light from one or more color light sources to the tooth for obtaining a polarized color reflectance image; calibrating the illumination uniformity and tooth shape; calculating a tooth shade for tooth restoration according to the images obtained; displaying a simulated image of the tooth using the calculated shade information; obtaining customer feedback on the displayed image; and sending or saving the tooth shade information.

A feature of the present invention is that it utilizes a common optical system for both diagnostic and cosmetic imaging. An advantage of the present invention is that it provides a single imaging instrument for a range of dental applications.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

FIGS. 9a and 9b show two embodiments of an attachment for capture of transmitted light;

DETAILED DESCRIPTION OF THE INVENTION

The method and apparatus of the present invention combine both diagnostic and cosmetic functions to provide a versatile intra-oral imaging system for use by dental practitioners. As noted earlier in the background section, there are significant differences in requirements between diagnostic and cosmetic imaging, including different light source and optical system requirements, appropriate compensation for specular reflection, and different image processing. Moreover, cosmetic imaging itself is complex and can involve more than merely shade matching. In addition to matching color, accurate cosmetic imaging also requires that additional information on more subtle tooth features be obtained, including translucency, surface texture, gloss, and other characteristics.

Commonly assigned U.S. Patent Application Publication No. 2007/0099148, previously mentioned and incorporated herein by reference, describes a diagnostic imaging approach that combines both fluorescence and reflectance effects in order to provide Fluorescence Imaging with Reflectance Enhancement (FIRE). Advantageously, FIRE detection can be accurate at an earlier stage of caries infection than has been exhibited using existing fluorescence approaches that measure fluorescence alone. The apparatus and methods of the present invention further expand upon the use of FIRE imaging, as described in detail in the '9148 application, in order to provide the added advantages of cosmetic imaging when using a single intra-oral camera.

Figure 1:
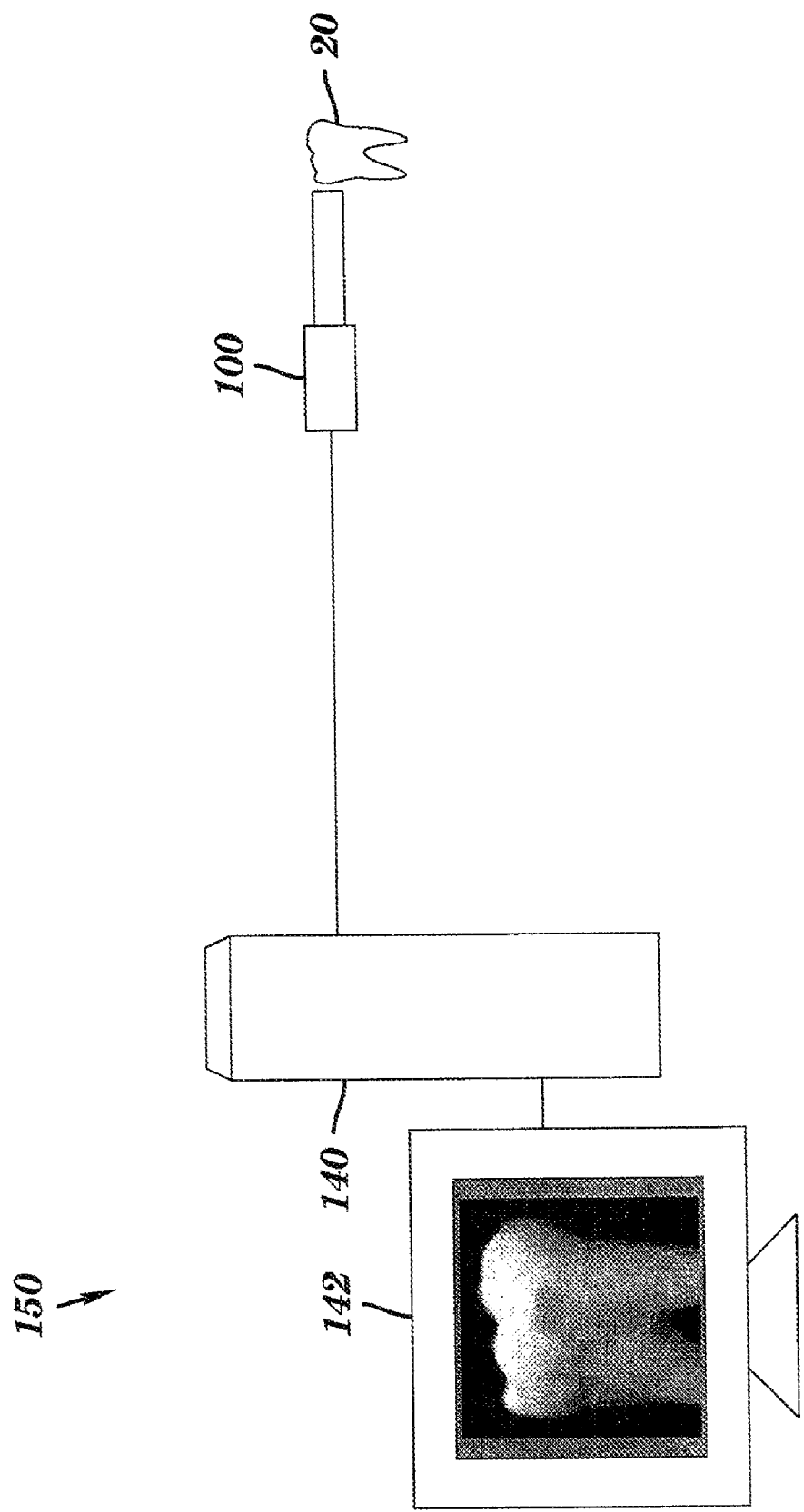
FIG. 1 is a schematic block diagram of an imaging apparatus for caries detection and shade matching according to one embodiment.

The schematic block diagram of FIG. 1 shows basic components of an imaging apparatus 150 for both diagnostic and cosmetic intra-oral imaging in one embodiment. An imaging probe 100 is used to obtain images from a tooth 20, either for diagnostic or cosmetic purposes. A control logic processor 140 communicates with probe 100 to obtain the image data and provides the processed image on a display 142.

Imaging apparatus 150 can operate in either of two modes: a diagnostic mode or a cosmetic imaging mode. Subsequent embodiments give examples showing how operation in either or both modes can be obtained using a suitable configuration of probe 100 and adapting the illumination, data collection, imaging processing, and data recording and display functions accordingly.

Figure 2:
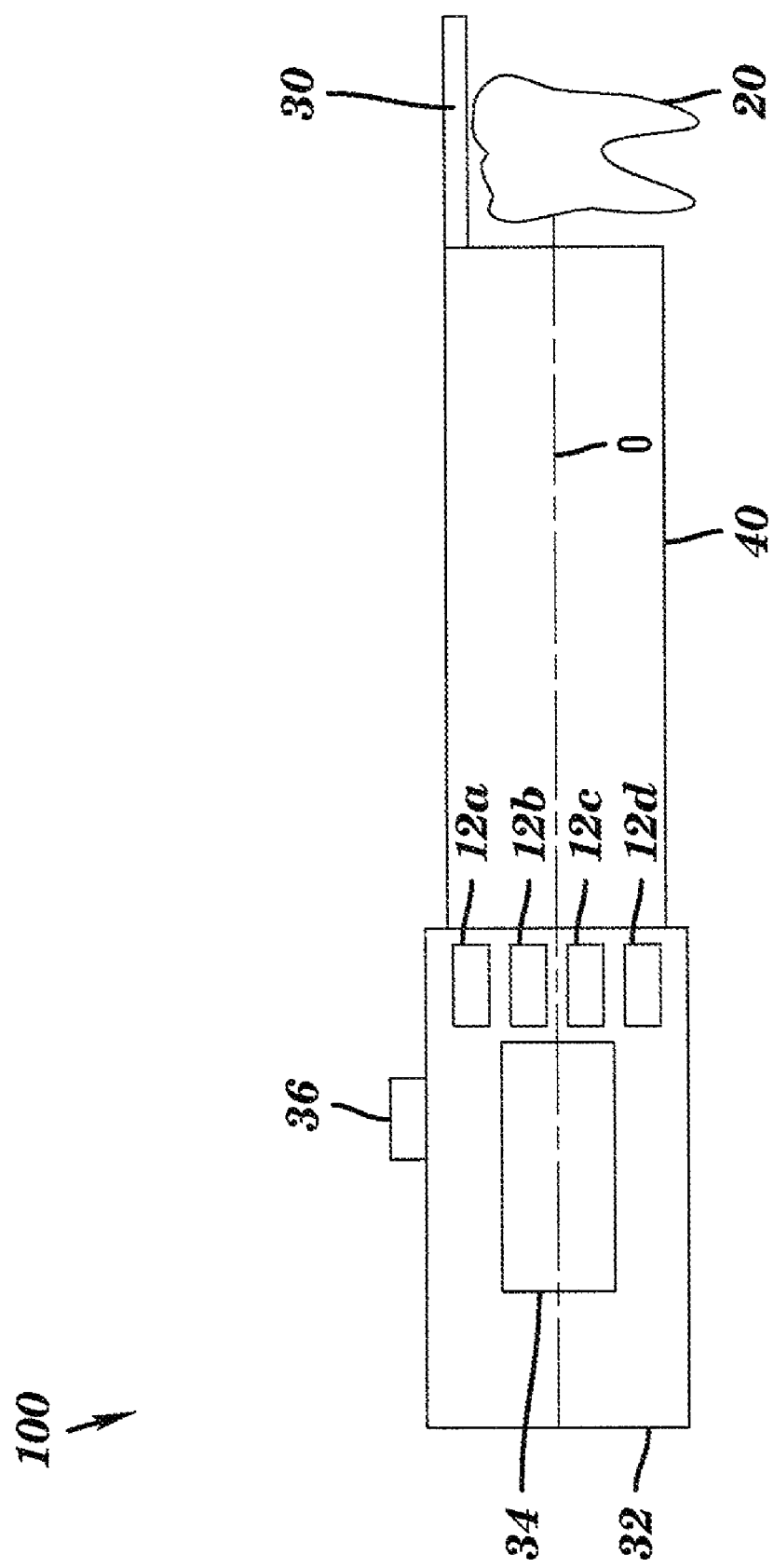
FIG. 2 is a schematic block diagram of an imaging probe for diagnostic and cosmetic imaging.

The schematic diagram of FIG. 2 shows an embodiment of imaging probe 100 that can be used for both diagnostic and cosmetic imaging purposes. Probe 100 has a handle 32 and a probe extension 40. A common optical axis O applies for both diagnostic and cosmetic image capture. Illumination for any type of image is provided from one or more of illumination apparatus 12a, 12b, 12c, or 12d, which include light sources and beam shaping optical elements. An optional attachment 30 provides illumination for translucency measurement. Probe 100 also includes a mode switch 36 which is used to select either of the operating modes: diagnostic or cosmetic. An imaging assembly 34 contains the imaging sensor and its supporting optical components, as described subsequently.

Each of illumination apparatus 12a-12d may have both light source and beam shaping optics. Each illumination apparatus could have its own light source, or a single light source could serve for multiple illumination apparatus 12a-12d, provided with an appropriate spectral selection filter for each illumination apparatus, for example. The light source could be a solid-state light source, such as a light emitting diode (LED) or laser, or could be a broadband light source such as xenon arc lamp or other type of light source.

Figure 3A:
FIGS. 3a to 3d show example schematic diagrams for different arrangements of components suitable for use as an illumination apparatus in embodiments of the present invention.
Figure 3B:
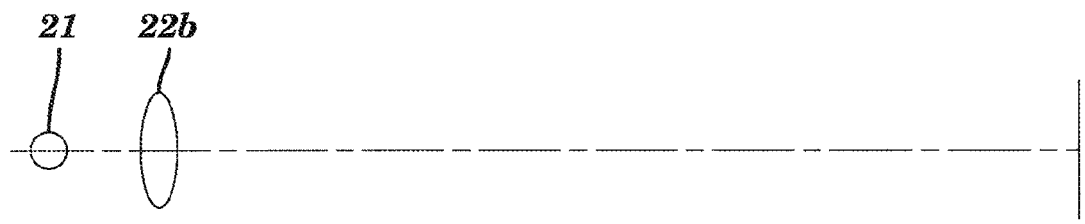
Figure 3C:
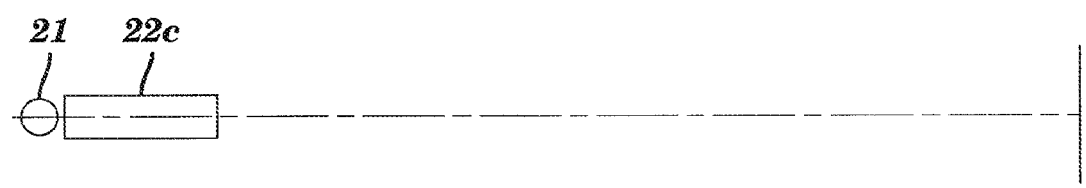
Figure 3D:
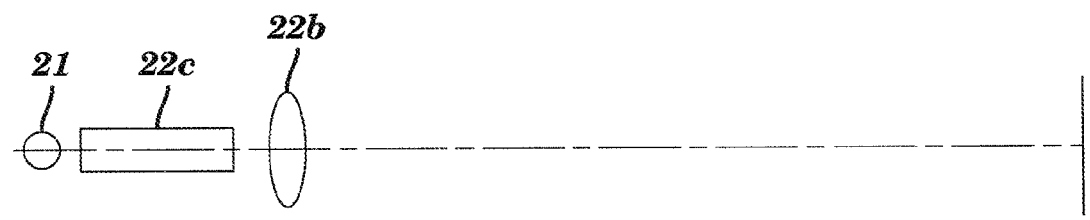

FIGS. 3a to 3d show example schematic diagrams for different arrangements of components that could be used for illumination apparatus 12a-12d in embodiments of the present invention. Each of these configurations has a light source 21. Beam-shaping optical elements 22, such as beam-shaping components 22a, 22b, or 22c condition and shape the light for uniform illumination on the tooth surface. If the beam profile from the light source is uniform enough for illumination on the tooth surface, no beam shaping optics are needed. Beam shaping component 22a of FIG. 3a is a diffuser. Beam shaping component 22b of FIG. 3b is a spherical or aspherical optical element. Beam shaping component 22c of FIG. 3c is a light pipe. FIG. 3d shows a configuration using a number of these different components in combination within an illumination apparatus. Other beam shaping components that are part of illumination apparatus 12a-12d can include light guiding or light distributing structures such as an optical fiber or a liquid light guide, for example (not shown). The light level is typically a few milliwatts in intensity, but can be more or less, depending on the light shaping and sensing components used.

Each illumination apparatus 12a-12d can be arranged in a number of ways, as shown in detail subsequently. Light source 21 for each illumination apparatus emits light with appropriate wavelengths for each different imaging mode. In one embodiment, for example, light source 21 in illumination apparatus 12a emits broadband visible light (400 nm-700 nm) for polarized reflectance imaging, or a combination from light sources with different spectrum, such as a combination of Red, Green and Blue light emitting diodes (LEDs). Light source 21 in illumination apparatus 12b emits narrow band ultraviolet (UV) light (375 nm-425 nm) to excite tooth fluorescence. Light source 21 in illumination apparatus 12c emits Near-Infrared (NIR) light for translucency measurement. Light source 21 in illumination apparatus 12d emits blue light or UV for tooth surface texture measurement. The light used in the illumination apparatus 12a can be also obtained from other sources, such as a daylight simulator.

Diagnostic Imaging Mode

Figure 4:
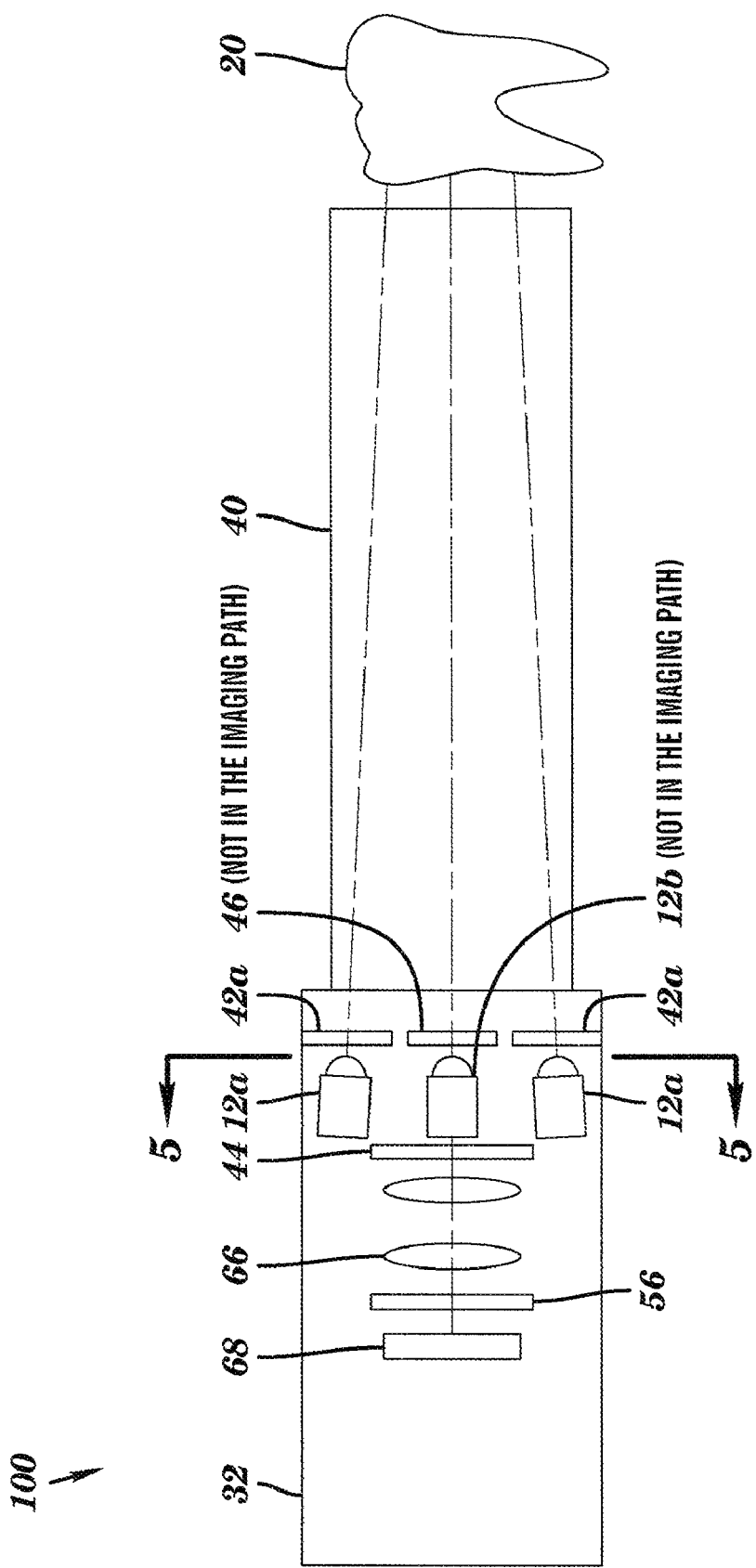
FIG. 4 is a schematic block diagram of an imaging probe configured for diagnostic imaging.
Figure 5:
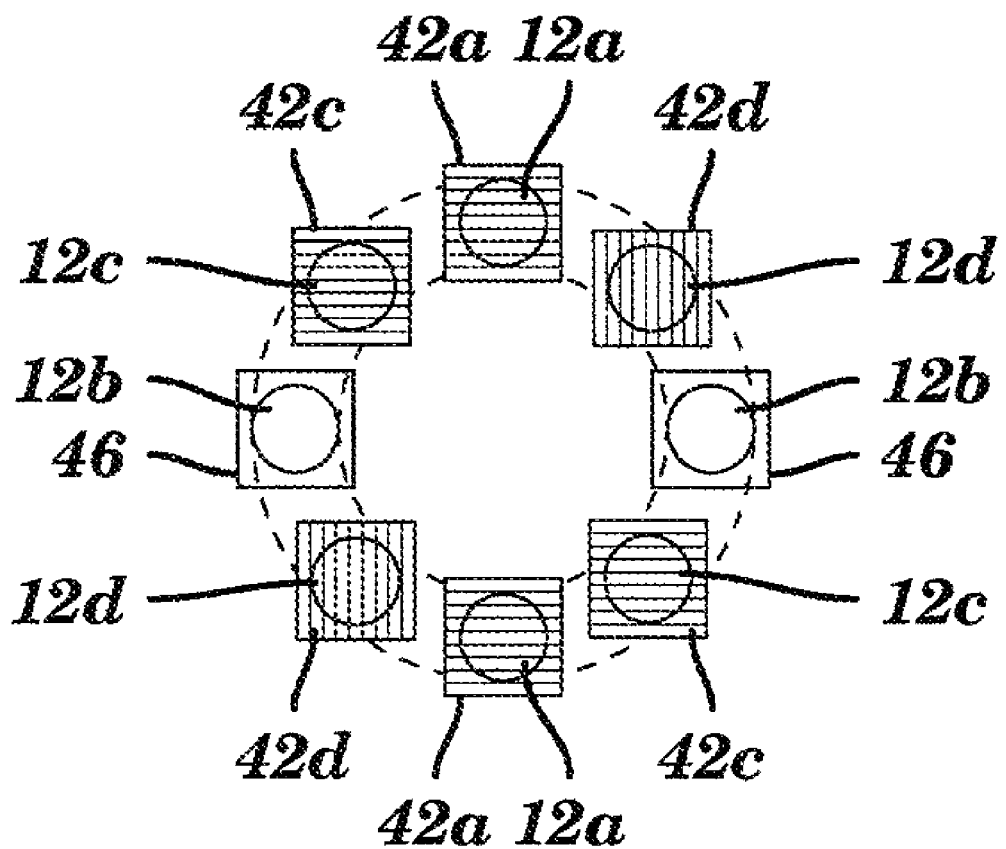
FIG. 5 shows, in a front view taken along line 5-5 of FIG. 4, one arrangement for multiple illumination apparatus used in the embodiment shown in FIG. 4.

The schematic diagrams of FIGS. 4 and 5 show probe 100 as configured for diagnostic imaging. Probe 100 has a handle 32 and a probe extension 40 that is designed for insertion into the mouth for both imaging modes. Illumination apparatus 12a, with the cooperation of polarizer 42a, which is placed in front of the illumination apparatus 12a, provides uniform polarized white light illumination on the tooth surface for polarized reflectance imaging. Illumination apparatus 12b directs UV light toward tooth 20 through a bandpass filter 46 to excite fluorescence in the tooth. Bandpass filter 46 is an option and is helpful for improving spectral purity of illumination from the light source in illumination apparatus 12b.

Light reflected from tooth 20 passes through a central opening among the illumination apparatus and through an analyzer 44. One or more lenses 66 then direct reflected light through a spectral filter 56. Spectral filter 56 has a long pass that captures fluorescence data over a range of suitable wavelengths and blocks the excitation light from the light source. In order to obtain a true color reflectance image, the cut-off wavelength of the spectral filter 56 is selected so that it can block the excitation light from illumination apparatus 12b, but not block the blue portion of the light from illumination apparatus 12a. The fluorescence image that has been obtained from tooth 20 can have a relative broad spectral distribution in the visible range, with light emitted that is outside the wavelength range of the light used for excitation. The fluorescence emission is typically between about 450 nm and 600 nm, while generally peaking in the green region, roughly from around 510 nm to about 550 nm. A sensor 68 obtains the fluorescence image, typically using the green color plane. However, other ranges of the visible spectrum could also be used in other embodiments. When taking fluorescence image, analyzer 44 can be moved out of the optical axis O if necessary to increase the fluorescence signal. Referring back to FIG. 1, this image data can then be transmitted back to control logic processor 140 for processing and display.

Still referring to FIGS. 4 and 5, polarized reflectance image data is also obtained using many of the same components. An illumination apparatus 12a directs visible light, such as a white light or other broadband light, through a polarizer 42a, and toward tooth 20. Analyzer 44, whose transmission axis is oriented orthogonally with respect to the transmission axis of polarizer 42, rejects light from specular reflection and transmits light used to form the reflectance image onto sensor 68. Filter 56 may be removed out of the optical axis O or replaced with another filter element as needed.

Sensor 68 may be any of a number of types of imaging sensing component, such as a complementary metal-oxide-semiconductor (CMOS) or charge-coupled device (CCD) sensor. Light sources used in illumination apparatus 12a and 12b can be lasers or other solid-state sources, such as combinations using one or more light emitting diodes (LEDs). Alternately, a broadband source, such as a xenon lamp having a supporting color filter for passing the desired wavelengths, could be used.

FIG. 5 shows one arrangement for multiple illumination apparatus used in the embodiment shown in FIG. 4. As FIG. 4 showed, probe 100 has multiple illumination apparatus 12a, 12b, 12c, and 12d. Illumination apparatus that have the same light spectrum are arranged to be symmetric to the optical axis of the imaging optics for a uniform illumination.

The imaging optics, represented as lens 66 in FIG. 4, could include any suitable arrangement of optical components, with possible configurations ranging from a single lens component to a multi-element lens. Clear imaging of the tooth surface, which is not flat but can have areas that are both smoothly contoured and highly ridged, requires that imaging optics have sufficient depth of field. Preferably, for optimal resolution, the imaging optics provides an image size that is suited to the aspect ratio of sensor 68.

Camera controls are suitably adjusted for obtaining each type of diagnostic image. For example, when capturing the fluorescence image, it is necessary to make appropriate exposure adjustments for gain, shutter speed, and aperture, since this image may not be intense. When sensor 68 is a color sensor, color filtering can be performed by color filter arrays (CFA) on the camera image sensor. That is, a single exposure can capture both back-scattered reflectance and fluorescence images. In one embodiment, the reflectance image is captured in the blue color plane; simultaneously, the fluorescence image is captured in the green color plane.

Image processing by imaging apparatus 150 (FIG. 1) combines the reflectance and fluorescence images in order to obtain a contrast-enhanced image showing caries regions, as is described in the '9148 Wong et al. application. Various methods can be used for processing, combining, and displaying the images obtained.

Figure 6:
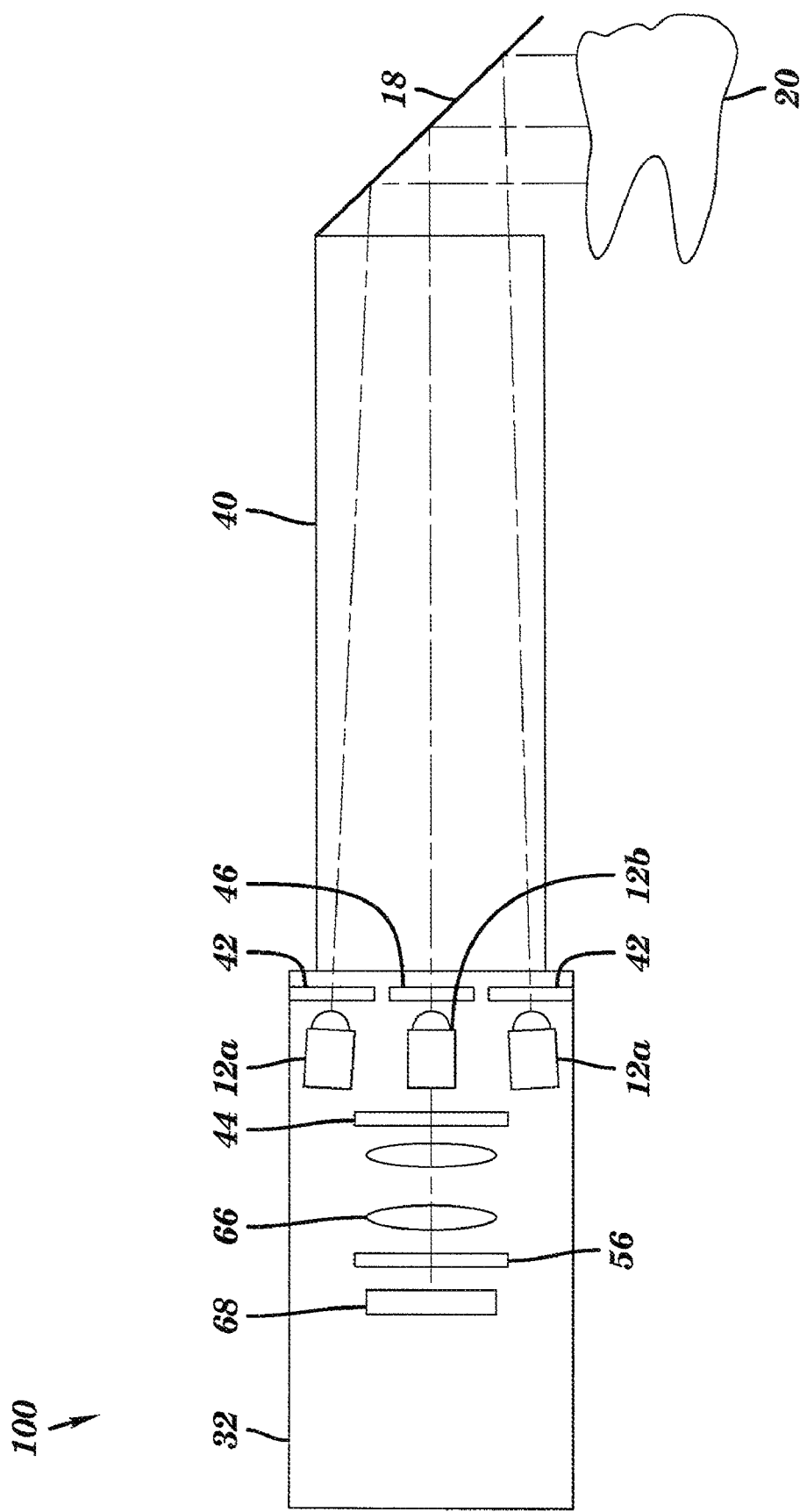
FIG. 6 shows an alternate embodiment of the imaging probe that employs a fold mirror for improved access to tooth surfaces.
Figure 7:
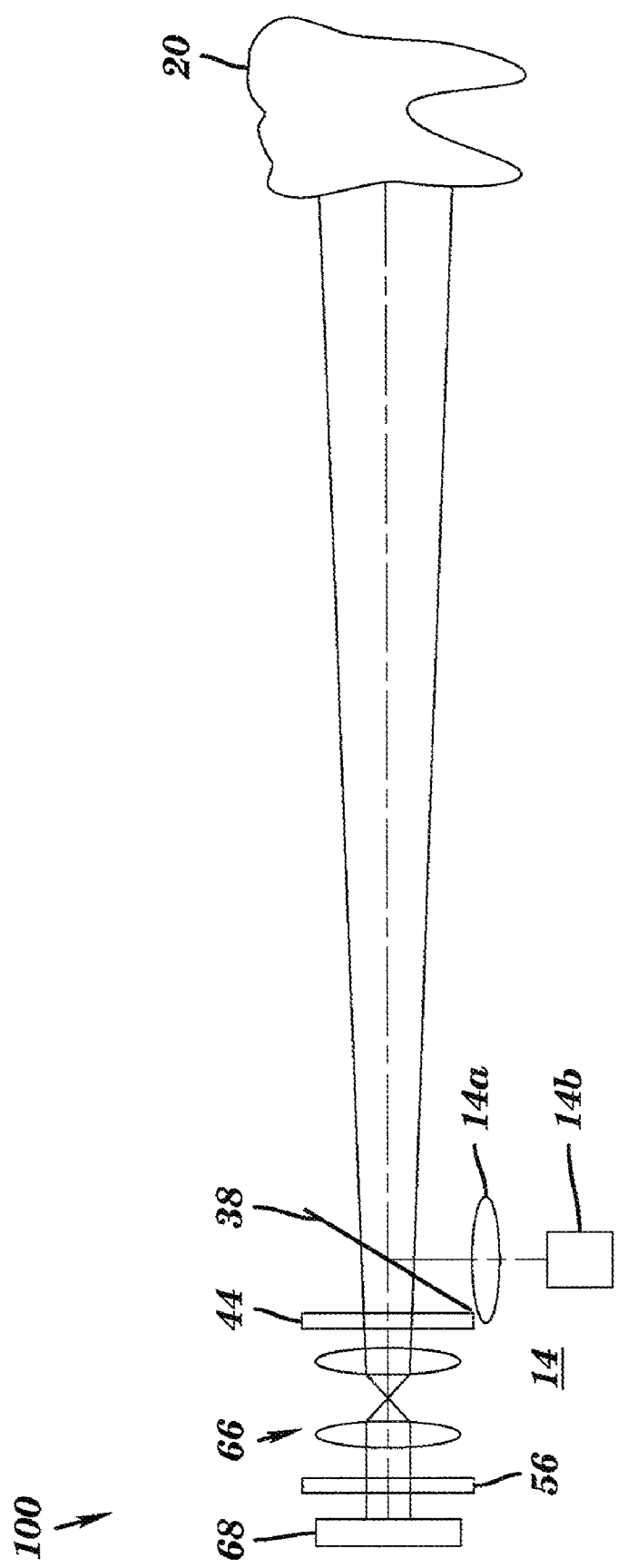
FIG. 7 shows another alternate embodiment of the diagnostic mode optical path using a polarization beamsplitter.

FIG. 6 shows an alternate embodiment of probe 100 that employs a fold mirror 18 for improved access to tooth 20 surfaces. This fold mirror is necessary in order to access the buccal surface of the molars and the occlusal and lingual surface of all teeth. FIG. 7 shows another alternate embodiment of the diagnostic mode optical path using a polarization beamsplitter 38. An illumination apparatus 14 provides light of one polarization directed through a beam shaping optical element 14a from a light source 14b, which is reflected from polarization beamsplitter 38 and directed toward tooth 20. Beam shaping optical element 14a shapes the light from an illumination apparatus 14 to provide uniform illumination on the tooth surface. Reflected light of the opposite polarization state is then transmitted through polarization beamsplitter 38 toward sensor 68. This arrangement removes specular reflected light from other scattered light, so that the returned light includes a high proportion of reflectance light from caries sites. Using the arrangement of FIG. 7, illumination apparatus 14 can be selected from a number of configurations, such as a combination of the light sources with different wavelengths or a single light source with spectrum selection filter. The light source 14b can also be outside of the handheld probe and the light delivered to the beam shaping optical element 14a through an optical fiber or other light guide such as a liquid light guide. One advantage of this embodiment is that illumination apparatus 14 can be easily changed to meet different applications. For example, illumination apparatus 14 can be changed to provide a daylight simulator for dental shade matching in cosmetic imaging mode, as is described subsequently.

Cosmetic Imaging Mode

When switched to cosmetic imaging mode, probe 100 operates under a different set of requirements. In this mode the illumination sources and optical path are suitably configured for the types of measurement that are of particular interest for cosmetic imaging. This includes the following:

(i) Color shade measurement;
(ii) Translucency measurement; and
(iii) Surface texture or gloss measurement.

In embodiments of the current invention, color shade measurement can be obtained using a number of approaches. In one approach, illumination is provided from polarized Red (R), Green (G), and Blue (B) light sources, sequentially. The resulting R, G, B images are then captured in sequence. The tooth shade can be calculated from the RGB images that are obtained. In an alternate approach, a polarized white light source is used as source illumination. The color shade of the tooth is then calculated from data in RGB planes of the white light image.

In one conventional method, unpolarized light is used in tooth shade measurement. One problem with unpolarized light illumination relates to specular reflection. The light from specular reflection has the same spectrum as the illumination light source and doesn't contain color information for the tooth. Additionally, very little surface information is obtained when specular reflection predominates and saturates the sensor.

By using polarized light illumination and specular reflection removal, embodiments of the present invention overcome this limitation and obtain scattered light from the enamel and dentin. This scattered light contains the true base color of the tooth.

Referring to FIGS. 4 and 5, when probe 100 of the present invention is used to measure tooth color, a broadband light source in illumination apparatus 12a is turned on. The broadband light from illumination apparatus 12a passes polarizer 42a and illuminates the tooth surface. Of all the light reflected back from the tooth, only the light having orthogonal polarization passes through analyzer 44 and reaches sensor 68. Tooth shade information is calculated from the R, G, and B plane data of sensor 68.

Because sensor and filter performance are imperfect, there is some amount of cross talk between each color plane when broadband illumination is used. An alternative solution for tooth color measurement is to obtain 3 separate images sequentially, each image separately illuminated using light of red, green, and blue spectra separately. These images can then be combined to produce more accurate tooth shade information. One disadvantage of this method is that it may require additional image processing in order to align the three different color images since they are taken at different time.

Figure 8A:
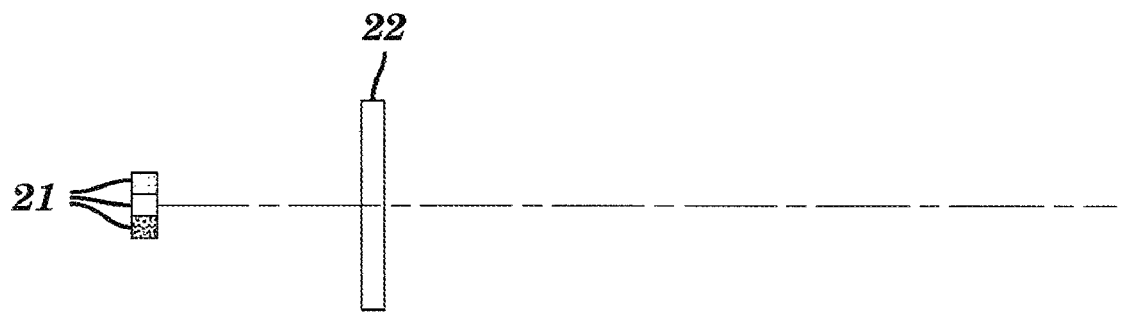
FIGS. 8a and 8b show two configurations for a color sequential illumination method.
Figure 8B:
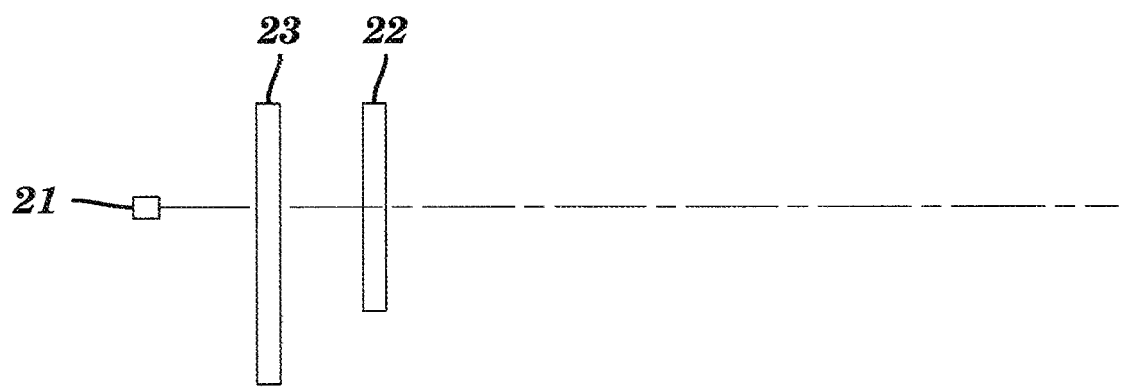

FIGS. 8a and 8b show two configurations for a color sequential illumination method. The first configuration of FIG. 8a comprises three light sources 21 such as red, green and blue LEDs, and one beam shaping optical element 22, which can be one of beam shaping elements 22a, 22b, or 22c, previously described or some combination of these elements. These three light sources can be switched either simultaneously or sequentially in order to obtain each of the composite Red, Green, and Blue images separately. The second configuration of FIG. 3b comprises a broadband light source 21, spectrum selection filter 23 and beam shaping optical element 22. While using this configuration, the spectrum selection filter 23 is rotated to change the illumination spectrum in order to obtain Red, Green and Blue images. Light source 21 and spectrum selection filter 23 of this embodiment can be built in or provided outside of probe 100. Illumination from these color sources could be directed to probe 100 by optical fiber or liquid light guide. This type of arrangement allows a wide selection of light sources, without the constraints imposed by size and weight limitations for probe 100.

The translucency of a tooth can be determined by measuring the reflectance light returned from the tooth or, alternately, the light transmitted through the tooth. The translucency can be used as a coordinate of the measurement point in one dimension of the shade space dedicated to this parameter. It can also be used for correction of at least one other coordinate of the measurement point in another dimension.

To use the reflectance light to determine tooth translucency, specular reflection must be removed either by changing the illumination angle, or by using polarized light illumination. One advantage of embodiments of the present invention using polarized light illumination relates to the light captured by the sensor and scattered in enamel and dentin. If unpolarized light is used, specular light reflected from the tooth surface and from the superficial layer of the enamel is much more pronounced than is the light returned from enamel and dentin. This can lead to inaccurate translucency data.

Theoretically, with the uniform illumination and ideal enamel, the tooth is more translucent if the light level of the polarized light, reflected from the tooth surface, and captured by the sensor 68, is lower. However, there are several factors that can affect the light level of the polarized light captured by the sensor 68. These factors include, for example, the thickness of the enamel, the local tooth defect, fillings, and local absorption. Therefore, calibration is an important process for translucency measurement. Also, in order to determine the translucency of the tooth from reflected light, calibration is necessary to correct the illumination non-uniformity and tooth shape factor. With calibration, one or more images captured for tooth color shade measurement, as discussed in a previous paragraph, can be processed to determine the tooth translucency. In one preferred embodiment, Near-Infrared (NIR) light is used for tooth translucency measurement since the scattering is weaker inside the tooth for light with longer wavelengths. In particular, the measurements taken in infrared light can be used for the correction of one coordinate of the measurement point in a dimension corresponding to the red shades. Illumination apparatus 12c and polarizer 42c in FIGS. 4 and 5 provide NIR light for translucency measurement.

When transmitted light is used to determine tooth translucency, the tooth is illuminated from the side opposite the image sensor. The illumination is not necessarily polarized, since there is no specular reflection in transmission mode. Translucency is determined by the light level transmitted through the tooth. A higher light level means that the tooth is more translucent.

Referring to FIGS. 9a and 9b, two embodiments of attachment 30 are shown. Either embodiment can be added to imaging probe 100 in order to capture transmitted light. In both embodiments, light from illumination apparatus 12a or 12c is delivered to a light output window 31 of attachment 30 by a light guide element. The light source, such as LEDs or other solid state light source, can also be placed directly in the light output window 31. In the embodiment of FIG. 9a, the light illuminates the tooth at an angle, as indicated by lines 33. In the embodiment of FIG. 9b, the light illuminates the tooth directly. In both embodiments, calibration on illumination uniformity is necessary when calculating the translucency from the transmitted light.

Another parameter of the tooth capable of being used as a coordinate of the shade space, or as a correction parameter, is the tooth's surface condition. This parameter is termed the roughness parameter, or texture. The roughness parameter can be used to establish one coordinate of the measurement point in one dimension of the shade space dedicated to this parameter. This can be determined by illuminating the tooth with light, and measuring the angular distribution and intensity of the light reflected from the tooth surface. A smooth tooth surface tends to return a greater amount of specularly reflected light. Since the scattering effect is stronger for light with shorter wavelength, blue or UV light source can be generally more advantageous for tooth surface texture or roughness measurement. Since the light reflected by the tooth surface and superficial enamel layer is more relevant to surface properties of the tooth, one strategy is to illuminate the tooth surface with polarized light, then to capture light of the same polarization state that is reflected from the tooth.

Again referring to the architecture of probe illumination shown generally in FIG. 4 and more particularly in FIG. 5, illumination apparatus 12d and polarizer 42d provide polarized light illumination for surface texture measurement. The light source in illumination apparatus 12d could be any light source in the spectral range from UV to NIR. In one preferred embodiment, UV or blue light is used, since the surface scatter effect is stronger. For surface roughness measurement, the orientation of polarizer 42d is orthogonal to that of other polarizers 42a and 42c in order to capture the light reflected back from the tooth surface with the same polarization as the illumination light. Polarizer 42d is not a requirement for surface roughness measurement and could be an option. Without polarizer 42d, light captured by the sensor is still polarized since there is an analyzer 44 in the imaging path. This polarized light contains both specular light and scattered light, since the illumination light is unpolarized. The analyzer 44 could be moved out of the optical axis too as needed for surface texture measurement.

As described earlier with reference to FIGS. 7 and 8, instead of separate light sources, beam shaping elements, and polarizers, a single broadband light source with one spectrum selection filter and one beam shaping element can also provide the needed illumination for color shade, tooth translucency, and surface roughness measurement.

Illumination uniformity is useful for determining both tooth translucency and surface roughness measurement. Any one of the illumination configurations shown in FIG. 3 could generate sufficiently uniform illumination. On the other hand, tooth shape is another factor which has a significant effect on the light level received by the sensor. For example, even with the same surface quality, the light level reflected back from the tilted surface is lower than that of the surface perpendicular with the optical axis. For these reasons, calibration for both illumination uniformity and surface shape is very important in order to obtain accurate measurement on tooth translucency and surface roughness.

ALTERNATE EMBODIMENTS

Figure 10:
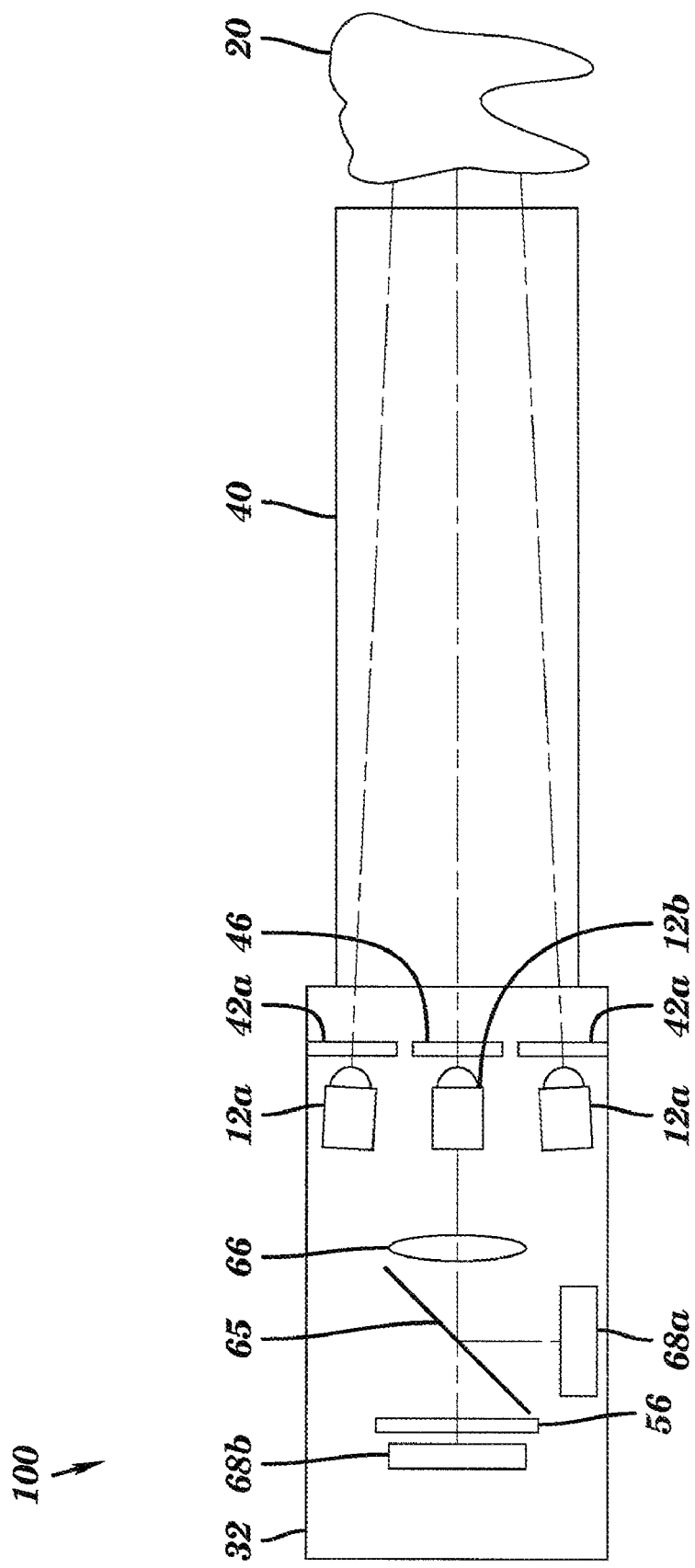
FIG. 10 shows an arrangement of probe 100 with two sensors.
Figure 11:
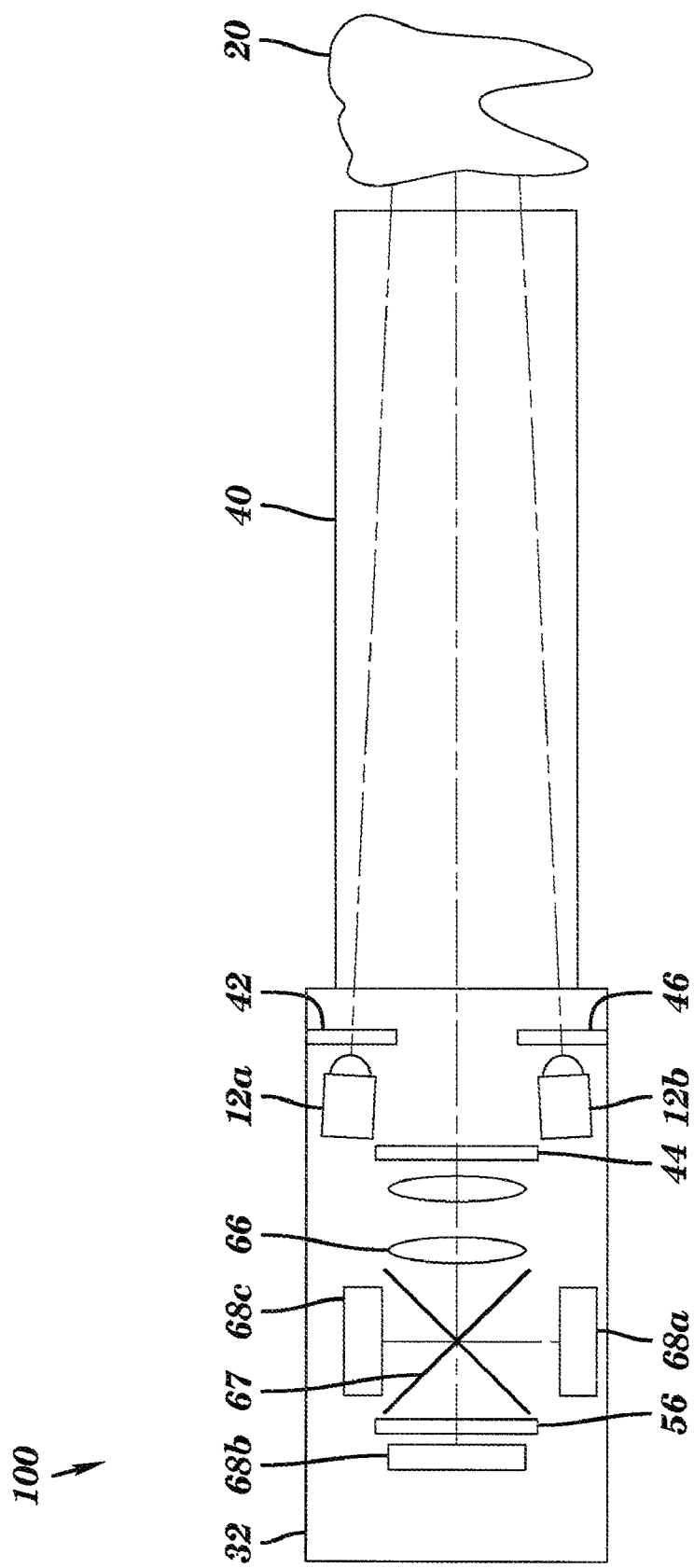
FIG. 11 shows an arrangement of probe 100 with three sensors.
Figure 12:
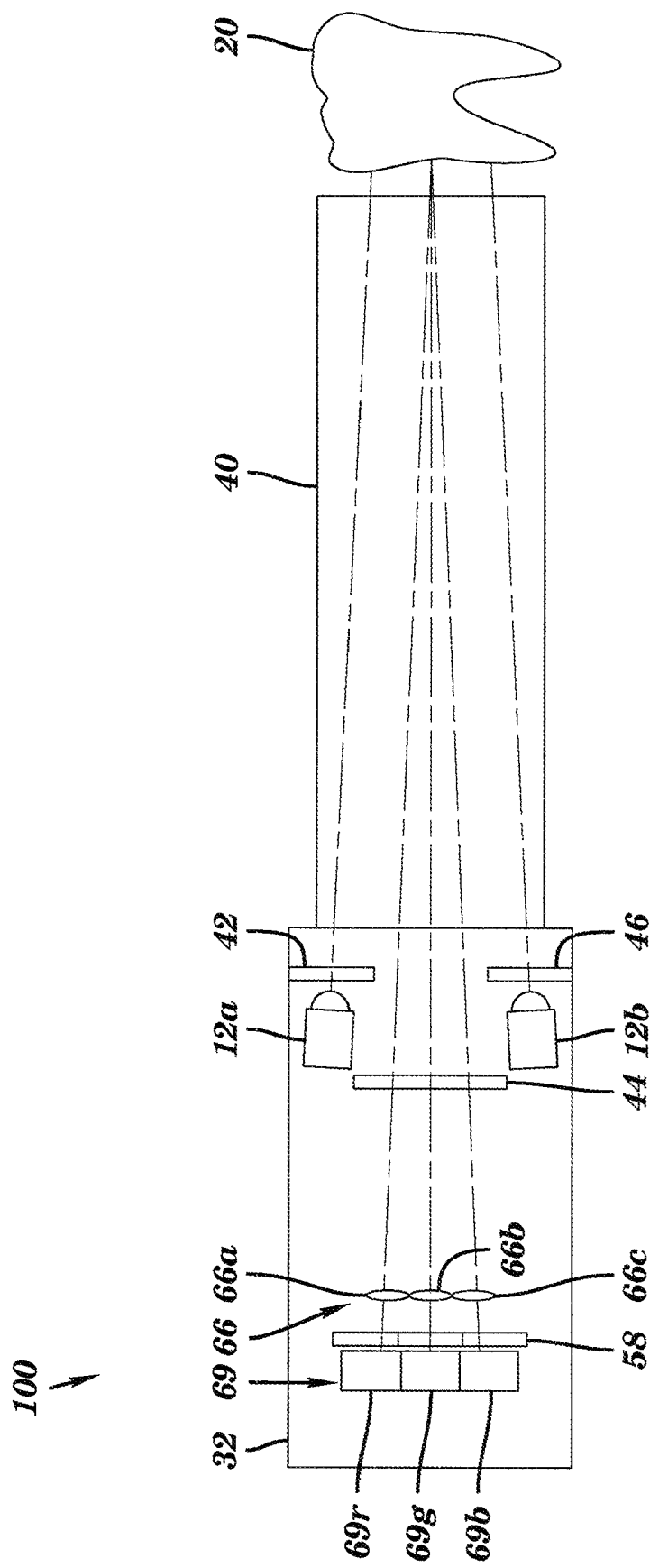
FIG. 12 shows an arrangement of probe 100 with three sensing regions.

FIGS. 10, 11, and 12 are alternative embodiments of probe 100 using more than one sensor. There are some benefits with more than one sensor, especially for an apparatus with diagnostic and cosmetic application modes. In FIG. 10, there are two sensors, 68a and 68b. A polarization beamsplitter 65 divides the light returned from the tooth into two parts having different polarizations. The light with orthogonal polarization goes to sensor 68a, while the light with the same polarization state goes to sensor 68b. A long pass filter 56 is placed in front of the sensor 68b to block the excitation light from illumination apparatus 12b. In diagnostic imaging mode, sensor 68b captures a fluorescence image and sensor 68a captures polarized white light image. In cosmetic imaging mode, the data from sensor 68b, which has the same polarization state as the illumination beam, can be used to determine the surface roughness. The data from sensor 68a is used to calculate the color shade and translucency.

The embodiment of probe 100 in FIG. 11 comprises three sensors, one for each color. A beam splitter element 67 separates the beam into three spectrum bands: UV to Blue band, Green band and Red to NIR band. One type of beam splitter element 67 that can be used is an x-cube that is configured to direct light to three sensors with different spectrum bands. As in FIG. 10, one long pass filter 56 is required in order to obtain fluorescence images without cross talk from the excitation light. Since there are Red, Green and Blue imaging data from three sensors separately, the calculated color shade is more accurate.

FIG. 12 is yet another alternate embodiment with three sensing regions 69r, 69g, and 69b in one sensor 69. Color filter 58 is placed in front of sensor 69 so that sensing regions 69r, 69g, and 69b capture the images in RED, Green and Blue regions. Since sensing regions 69r, 69g, and 69b are in the same plane, three separate imaging lenses 66a, 66b, and 66c are necessary.

Figure 13:
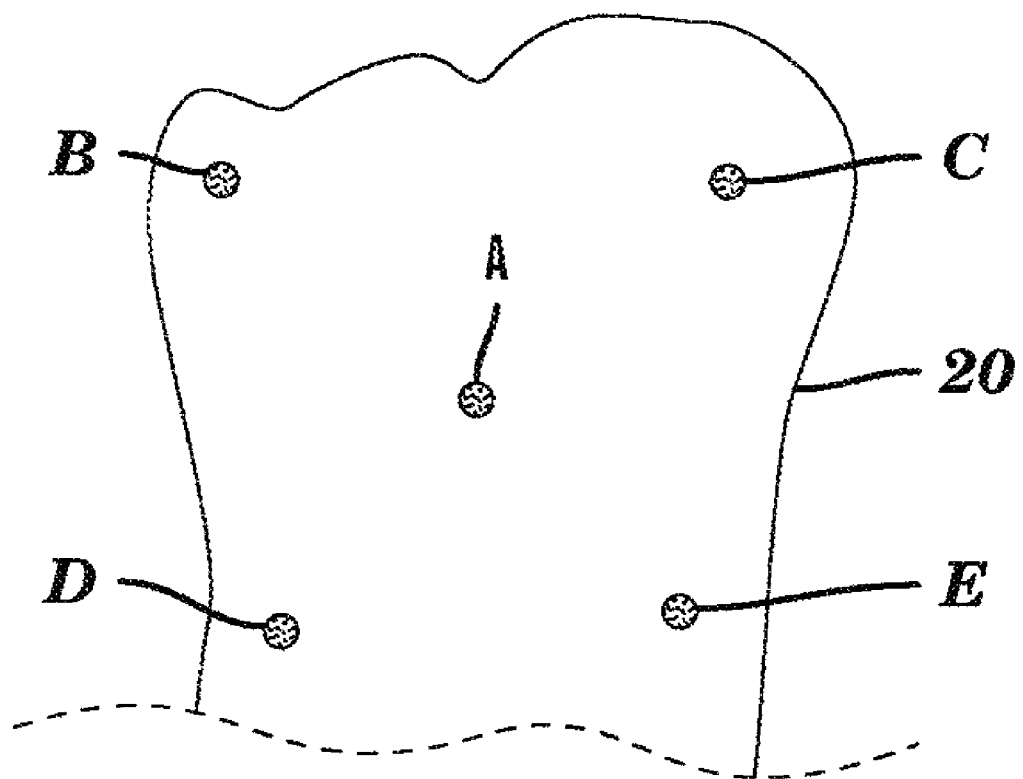
FIG. 13 shows a point-based method for measuring tooth translucency.

FIG. 13 shows another point-based method for measuring tooth translucency and surface roughness. As shown in this figure, a number of individual points, shown as A, B, C, D and E, are illuminated with polarized light. The sensor captures the tooth surface image formed by the orthogonal polarized light reflected from these points. The method illustrated in FIG. 13 works as follows: After the illumination light reaches the enamel, it scatters inside the tooth randomly and exits the tooth surface from all over the tooth surface. Even when the tooth is not illuminated over its entire surface, the sensor can still obtain the tooth image with sufficient scattered light. This image gives a particularly good characterization of tooth properties, such as tooth translucency and surface roughness. It should be emphasized that FIG. 13 only presents a point illumination method. Other illumination methods, such as grid illumination and line illumination, can be applied and can offer similar advantages.

Operation of Imaging Apparatus 150

Figure 14:
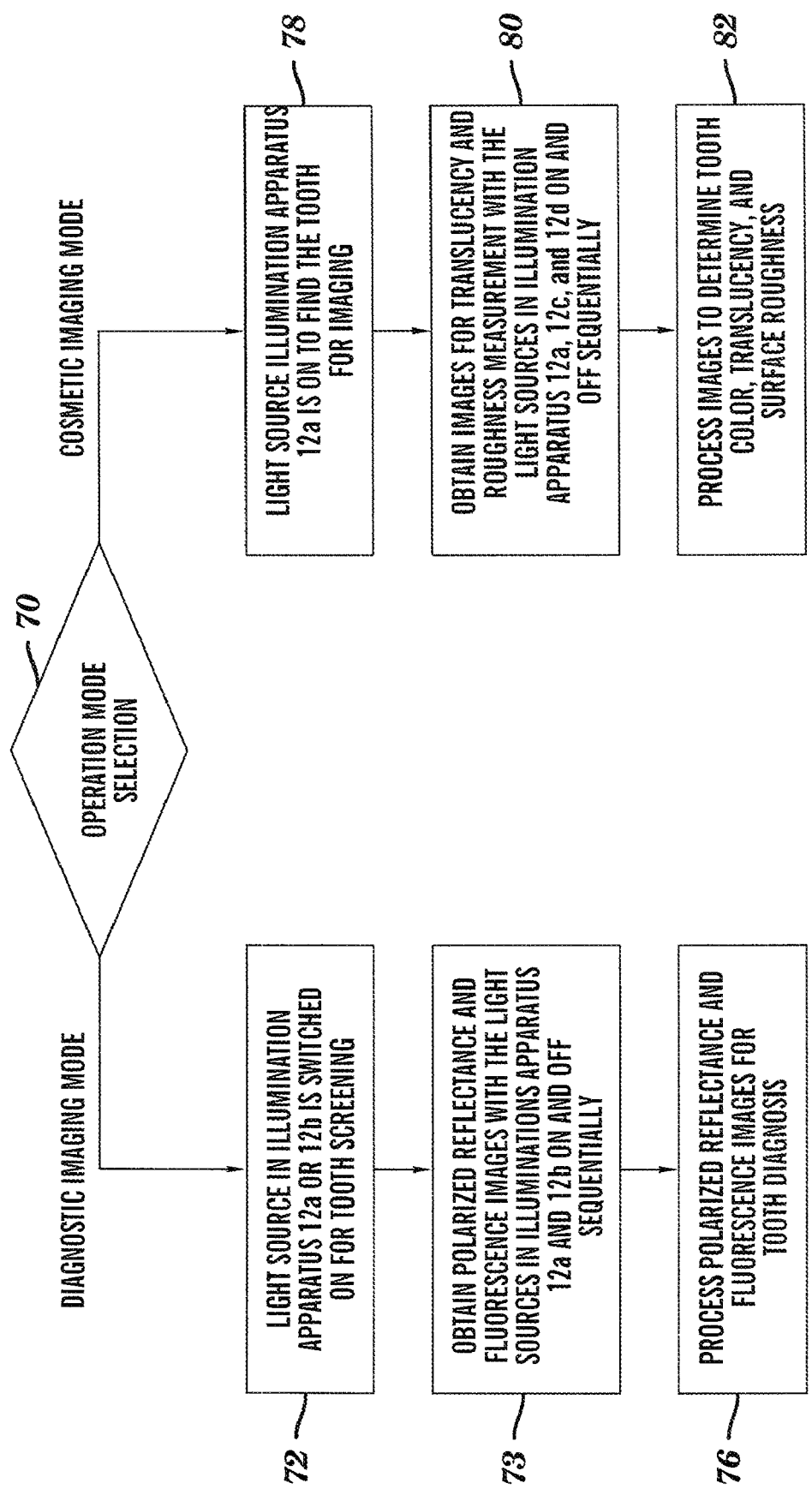
FIG. 14 is a logic flow diagram showing how the imaging apparatus of the present invention can be operated in either diagnostic or cosmetic modes.

Imaging apparatus 150 is designed to obtain translucency, surface texture, and color shade measurements as well as to obtain images for dental caries detection. FIG. 14 is a logic flow diagram showing how this apparatus can be operated in either mode. Initially, an operation mode selection 70 is made, such as by actuating mode switch 36. In diagnostic imaging mode, the light source in illumination apparatus 12a or 12b is turned on for tooth examination (step 72). When the operator decides to capture the images and pushes the shutter (or otherwise enters the command to capture the image), the light sources in illumination apparatus 12a and 12b are switched on and off sequentially for sensor 68 to capture the polarized reflectance image and fluorescence image (step 73). Then the image processing software processes the images and provides the analyzed data (step 76). Software suitable for this purpose is disclosed in commonly assigned, copending U.S. patent application Ser. No. 11/623,804, previously mentioned, the contents of which are incorporated by reference into this specification.

With the selection of cosmetic imaging mode, the light source in illumination apparatus 12a is turned on to determine the right teeth for imaging (step 78). To take images for color shade, translucency and texture measurement, the light sources in illumination apparatus 12a, 12c, and 12d (or light source 31) are turned on and off sequentially (step 80). The final step 82 is to calculate, using image analysis techniques known to those skilled in the art, the tooth color shade, translucency, and roughness from the images obtained in step 80.

Figure 15:
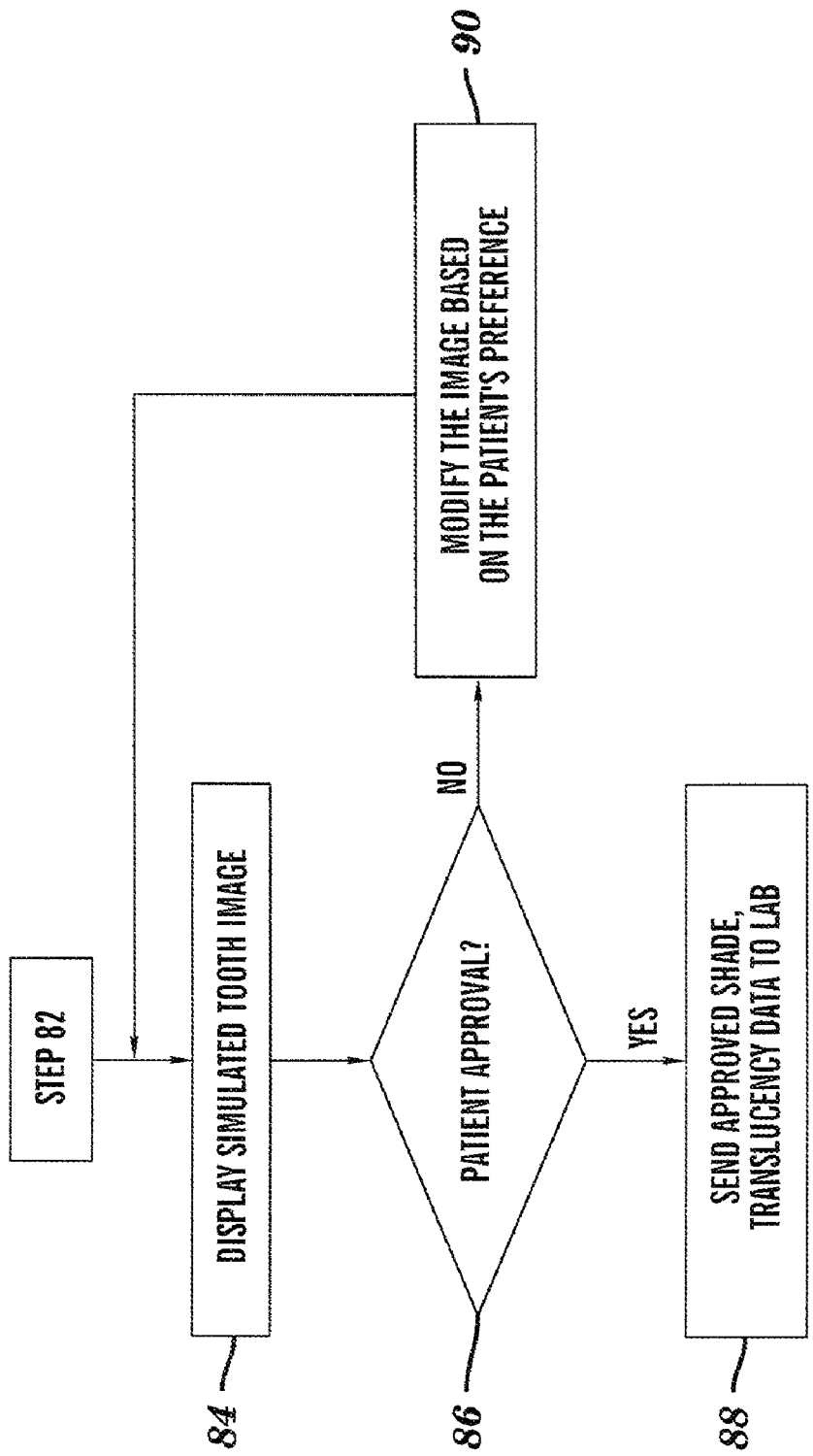
FIG. 15 is a logic flow diagram that shows how processor logic uses the translucency and color data obtained in the process of FIG. 14 to provide shade matching.

The logic flow diagram of FIG. 15 shows how processor logic uses the translucency and color data obtained in the process of FIG. 14 to provide shade matching. After the tooth shade, translucency and surface roughness are calculated (step 82), the image processing software displays a simulated tooth to the patient for review (step 84). A patient approval step 86 then prompts the patient to approve the calculated shade, using a simulation provided on display 142 (FIG. 1). When approved, the data is sent to a lab or other processing facility (step 88). If not, the image process software will modify the simulated image based on the patient's preference (step 90), and re-display the modified image to the patient for approval.

Figure 16:
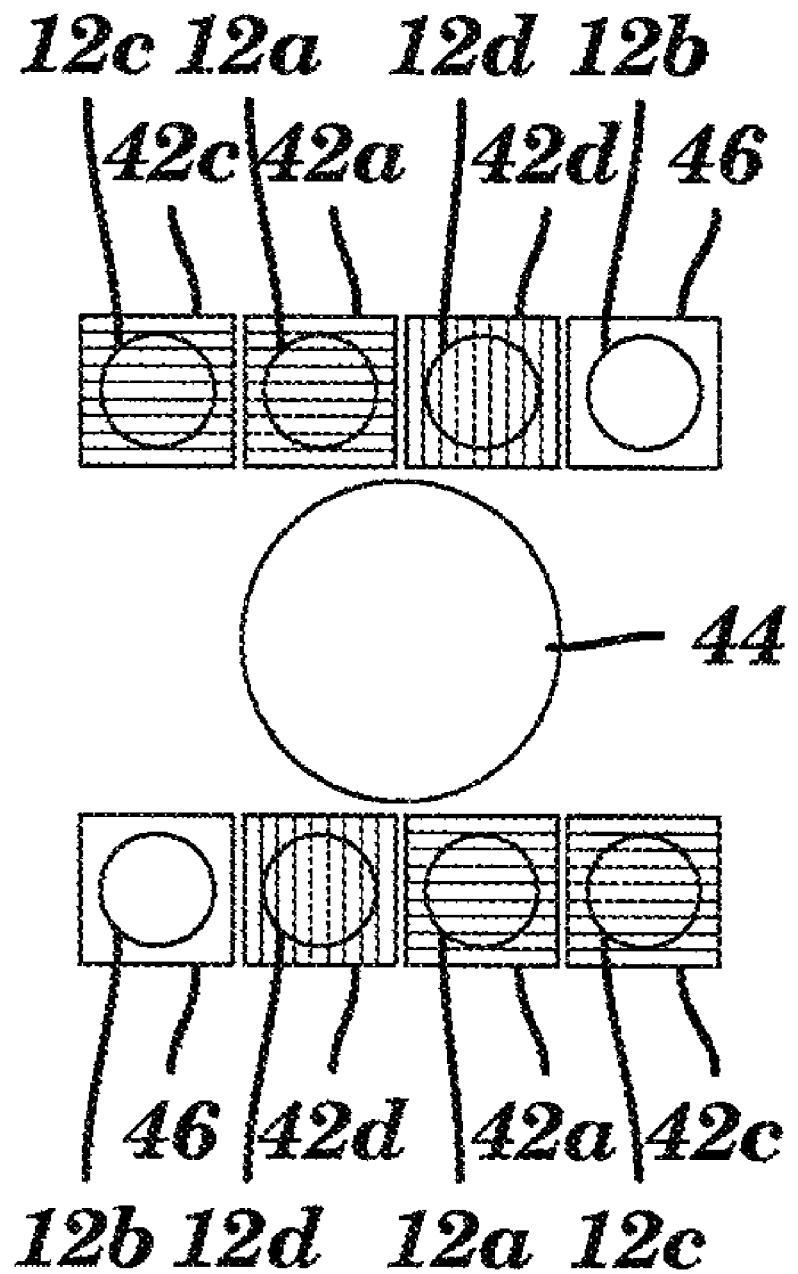
FIG. 16 shows an alternative arrangement of light sources suitable for use in the apparatus of the invention.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, various arrangements of light sources in illumination apparatus 12a-d could be used, with various different embodiments employing a camera or other type of image sensor, such as the parallel arrays of light sources shown in FIG. 16.

Thus, what is provided is a dental imaging apparatus that provides, in a single unit, diagnostic imaging for caries detection and cosmetic imaging for shade mapping.

PARTS LIST 12, 12a, 12b, 12c, 12d. Illumination apparatus
14. illumination apparatus
14a. Beam shaping optical element
14b. light source
18. Fold mirror
20. Tooth
21. Light source
22. Beam shaping optical element
22a. Diffuser
22b. Beam shaping element
22c. Light guide
23. Spectrum selection filter
30. Attachment for translucency measurement
31. Light output window
32. Handle
33. Light lines
34. Imaging assembly
36. Mode switch
38. Polarization beamsplitter
40. Probe extension
42, 42a, 42c, 42d. Polarizer
44. Analyzer
46. Bandpass filter
56. Long pass spatial filter
58. Color filter
65. Polarization beamsplitter
66, 66a, 66b, 66c. Lens
67. Beamsplitter
68, 68a, 68b, 68c. Sensor
69. Sensor
69r, 69g, 69b. Sensor regions
70, 72, 73, 76, 78, 80, 82, 84, 86, 88, 90. Method steps
100. Imaging probe
140. Control logic processor
142. Display
150. Imaging apparatus
A, B, C, D, E. illumination points
O. Optical axis

The invention claimed is:

1. An apparatus for obtaining images of a tooth, comprising:
   a) at least one image sensor disposed along an optical axis, the image sensor comprising common optical components for both diagnostic and cosmetic imaging;
   b) at least one broadband polarized illumination apparatus for reflectance imaging;

c) a narrow-band ultraviolet illumination apparatus for fluorescence imaging;
d) a near IR band polarized illumination apparatus for translucency imaging;
e) one of a blue or UV band polarized illumination apparatus for texture imaging, the polarization orthogonal to polarization of the broad band illumination apparatus and the near IR band illumination apparatus;
f) one or more polarization elements disposed along the optical axis to eliminate specular reflection;
g) a filter disposed along the optical axis to block narrow-band ultraviolet light; and
h) a switch for selecting one of the operation modes of diagnostic imaging using reflectance and fluorescence imaging, and cosmetic imaging using reflectance imaging, translucency imaging, and texture imaging.

2. The apparatus of claim 1, wherein cosmetic imaging further uses light transmission through the tooth.

3. The apparatus of claim 2 further comprising an attachment for illuminating the occlusal or lingual surface to obtain an image from the transmitted light.

4. The apparatus of claim 3 wherein the attachment comprises a light guide.

5. The apparatus of claim 3 wherein the attachment comprises a light source and a beam-shaping element.

6. The apparatus of claim 5 wherein the light source is a near-infrared light source.

7. The apparatus of claim 1 wherein the broadband illumination apparatus comprises at least one light source with the spectrum from 400 nm to 700 nm.

8. The apparatus of claim 1 wherein the broadband illumination apparatus further comprises one or more beam shaping elements.

9. The apparatus of claim 1 wherein the narrow-band ultraviolet illumination apparatus comprises at least one narrow-band ultraviolet light source with the spectral range of 375 nm to 425 nm.

10. The apparatus of claim 1 wherein the narrow-band ultraviolet illumination apparatus further comprises a band-pass filter to clean the spectrum of the narrow-band ultraviolet light source.

11. The apparatus of claim 1 wherein the polarization element is a polarization beamsplitter.

12. The apparatus of claim 1 wherein the polarization element is a plate polarizer.

13. The apparatus of claim 1 wherein there are two image sensors, further comprising a polarization beam splitter to separate the light with different polarization states to two sensors.

14. The apparatus of claim 1 wherein there are two image sensors, further comprising at least one dichroic mirror to separate the light with different spectral ranges to at least two sensors.

* * * * *